United States Patent
Houghton et al.

(10) Patent No.: US 9,551,649 B2
(45) Date of Patent: Jan. 24, 2017

(54) SURFACE SAMPLING METHOD, DEVICE, AND SYSTEM FOR ENHANCED DETECTION OF CHEMICAL AND BIOLOGICAL AGENTS

(71) Applicant: SRC, Inc., North Syracuse, NY (US)

(72) Inventors: Stephen R. Houghton, Tully, NY (US); Marc P. Roberts, Alexandria, VA (US); Nicole J. Surace Clayton, Liverpool, NY (US); James W. McLean, Cicero, NY (US); Robert M. Cannon, Clay, NY (US)

(73) Assignee: SRC, INC., North Syracuse, NY (US)

( * ) Notice: Subject to any disclaimer, the term of this patent is extended or adjusted under 35 U.S.C. 154(b) by 118 days.

(21) Appl. No.: 14/723,628

(22) Filed: May 28, 2015

(65) Prior Publication Data

US 2016/0349172 A1    Dec. 1, 2016

(51) Int. Cl.
| | |
|---|---|
| *G01J 3/44* | (2006.01) |
| *G01N 21/03* | (2006.01) |
| *G01N 1/10* | (2006.01) |
| *G01N 33/22* | (2006.01) |
| *G01N 21/65* | (2006.01) |
| *G01N 1/02* | (2006.01) |

(52) U.S. Cl.
CPC ............ *G01N 21/0303* (2013.01); *G01N 1/10* (2013.01); *G01N 21/65* (2013.01); *G01N 33/227* (2013.01); *G01N 2001/027* (2013.01); *G01N 2001/028* (2013.01); *G01N 2201/06113* (2013.01)

(58) Field of Classification Search
CPC .......... G01N 21/03; G01N 21/65; G01N 1/10; G01N 33/22; G01J 3/44
See application file for complete search history.

(56) References Cited

U.S. PATENT DOCUMENTS

| | | | |
|---|---|---|---|
| 5,364,792 A | 11/1994 | Stone | |
| 5,550,061 A | 8/1996 | Stone | |
| 5,956,123 A * | 9/1999 | Abe | ............ A61F 2/0095 351/216 |
| 8,388,907 B2 | 3/2013 | Gold et al. | |

(Continued)

FOREIGN PATENT DOCUMENTS

| | | |
|---|---|---|
| JP | 2000344536 | 12/2000 |
| WO | 2009105009 | 8/2009 |

OTHER PUBLICATIONS

Farquharson et al. "Chemical agent identification by surface-enhanced Raman spectroscopy" Proceedings of SPIE, 2002, 4577, pp. 166-173.

(Continued)

*Primary Examiner* — Abdullahi Nur
(74) *Attorney, Agent, or Firm* — Bond Schoeneck & King, PLLC; George McGuire

(57) ABSTRACT

A system, method, and device for analyzing a sample using spectroscopy. The system includes a spectroscope, a sample vial with a swab removably sealable within a transparent enclosure, the swab including an absorbent collection substrate. The system further includes a sample vial adaptor configured to affix to the spectroscope, and a sample vial receptacle that receives the sample vial. The adaptor is configured to position the sample vial such that the transparent portion of the enclosure is between the swab and the laser of the Raman instrument, and such that the swab is positioned at the focal distance of the laser.

31 Claims, 16 Drawing Sheets

(56) References Cited

U.S. PATENT DOCUMENTS

| | | |
|---|---|---|
| 8,414,846 B2 | 4/2013 | Gold et al. |
| 8,665,433 B2 | 3/2014 | Da Re et al. |
| 2011/0014718 A1 | 1/2011 | Haas et al. |
| 2012/0028372 A1 | 2/2012 | Han et al. |
| 2012/0231550 A1 | 9/2012 | Roy et al. |
| 2013/0043130 A1 | 2/2013 | Lednev et al. |
| 2013/0114070 A1 | 5/2013 | Gardner, Jr. et al. |
| 2013/0135609 A1 | 5/2013 | Gardner, Jr. et al. |
| 2013/0213154 A1 | 8/2013 | Crowder et al. |
| 2014/0093645 A1 | 4/2014 | Thimsen et al. |
| 2014/0118731 A1 | 5/2014 | Ayers |
| 2014/0118733 A1 | 5/2014 | Harward |

OTHER PUBLICATIONS

Hunt et al. "Computer Assisted Robotic Examination Swab Sampling (CARESS)", Proceedings of SPIE, 2008, 6962, pp. 696200-1-696200-9.

Lewis et al. "Raman spectroscopic studies of explosive materials: towards a fieldable explosives detector", Spectrochimica Acta Part A, 1995, 51, pp. 1985-2000.

Nagli et al. "Raman scattering spectroscopy for explosives identification" Proceedings of SPIE, 2007, 6552, pp. 65520Z-1-65520Z-10.

* cited by examiner

SURFACE SAMPLING METHOD, DEVICE, AND SYSTEM FOR ENHANCED DETECTION OF CHEMICAL AND BIOLOGICAL AGENTS

FIELD OF THE INVENTION

The present disclosure is directed generally to methods, devices, and systems for the collection and detection of chemical and biological agents, and more specifically to methods, devices, and systems for augmenting the detectability of liquid and solid phase chemical hazards and signatures, allowing for enhanced detection sensitivity of chemical and/or biological agents in a field-deployed setting in near real-time.

BACKGROUND

There is an increasing demand for methods and systems capable of detection, quantitative characterization, and notification of the presence of chemical, biological, radiological, nuclear, and/or explosive ("CBRNE") hazards across a broad range of disciplines, including defense, food safety, homeland security, and medical diagnostics, among many others. For example, rapid screening of unknown liquids and solids on surfaces for low levels of chemical warfare agents ("CWA"), toxic chemicals, narcotics, and explosives in the field is a critical capability need for assuring the safety of warfighters, law enforcement officials, emergency responders, and homeland security officials, among others. Rapid field detection and identification of CBRNE hazards enables an appropriate response and accurate decision making that facilitates time and cost savings as well as proper protective measures. In addition, mitigation of surfaces contaminated with CWAs, some toxic chemicals, and biological toxins is particularly imperative given that lethal doses can occur from dermal exposures of just a few milligrams or less.

While there is existing technology for the detection and identification of chemical and biological hazards on surfaces, these sensors often require a substantial quantity of target analyte to detect and identify the hazard directly on the surface due to interfering background signal from the surface itself. In addition, direct interrogation of chemical and biological materials on the surface may require risk of contamination of the sensor and or personnel. In the case of explosive residues, interrogating of large amounts of target analyte using laser-based spectroscopic methods such as Raman can risk detonation which could injure personnel and/or damage expensive sensors. Therefore, mechanisms to minimize the required amount of target analyte are advantageous to reduce exposures and protect personnel while still providing accurate and rapid characterization. Further, existing surface detection instruments are unable to achieve sufficiently sensitive results in a rapid manner with little or no sample preparation. Analyses requiring sample preparation are time consuming, can be error prone, and may effectively dilute the target analyte resulting in a lower concentration and reduced likelihood of achieving detection. Accordingly, there is a continued need for rapid, accurate, and reliable portable sensor systems capable of being deployed in the field.

One method used for the identification of biological or chemical threats is Raman spectroscopy. Raman is a form of vibrational spectroscopy proven to exhibit excellent selectivity for the purpose of material identification and has been the handheld liquid/solid analyzer of choice for defense and homeland security applications. Raman spectroscopy utilizes a monochromatic laser to interrogate unknown samples. Depending on the specific wavelength of light, the composition of the background material, and properties of the chemical being interrogated, the light can result in absorption, transmission, reflection, or scattering. Light that is scattered from the sample can result in either elastic collisions resulting in Raleigh scattering or inelastic collisions resulting in Raman scattering. Raman light scattering is the result of a photon exciting the molecule through vibration and rotation of its bonds from a ground state to a virtual energy state. Once the molecule relaxes, it emits a photon and returns to a rotational or vibrational state different from the original ground state. The energy delta between these levels results in a shift of the emitted photon's frequency away from the excitation wavelength. The result is a detection method based on the peak intensities at characteristic shifts measured in wavenumber (cm−1) or wavelength (nm) and attributed to specific molecules, thus generating a Raman spectral "fingerprint" by recording the intensity of light as a function of the energy difference between the laser and Raman scattered light. This output is reproducible and allows development of identification algorithms for the spectral fingerprints.

One difficulty with existing Raman detectors is that some background surfaces undergo a competing phenomenon, referred to as fluorescence, which can mask the signal of the target analyte since it is often several orders of magnitude more intense than Raman scattering. For example, highly colored surfaces, plastics, and surfaces with organic binders, paints, and adhesives can obscure a Raman signal and affect the sensitivity of analysis. Modulation of the wavelength of the incident light can alleviate some fluorescence effects, but most fielded instruments operate at a static incident laser wavelength chosen to balance these effects as well as to conserve power, weight, and complexity of the device. The sensor wavelength can be increased to minimize fluorescence but Raman signal diminishes as the $4^{th}$ power of laser wavelength. Therefore, a Raman sensor at an excitation wavelength of 1064 nm has a signal approximately 3.4 times weaker than a corresponding sensor at a wavelength of 785 nm. Accordingly, for these and other reasons, existing Raman detectors are not sensitive enough to detect low levels of chemical and biological agents. Enabling a surface sampling method, device, and system capable of concentrating the target analyte to maximize the detector signal, while also reducing background interference can consequently dramatically improve sensor sensitivity and selectivity.

Accordingly, there is a continued need for surface sampling methods, devices, and systems to augment the sensitivity of existing detectors in order to provide detection of chemical and/or biological agents in a field-deployed setting in near real-time.

SUMMARY OF THE INVENTION

The present disclosure is directed to a surface sampling method, device, and system for detecting and identifying one or more chemical and/or biological agents in the field. The invention comprises a system for analyzing a sample using Raman spectroscopy or another analytical device such as FTIR, among many others. According to an embodiment, the system includes a Raman spectroscope configured to obtain Raman spectral data from a target analyte, a sample swab used to obtain the target analyte, a sample vial, and an adaptor which properly positions the sample vial such that a transparent portion of the enclosure is between the laser and the sample swab, and such that the sample swab is positioned at the optimized focal distance of the laser.

In some embodiments, the method comprises greatly improved fielded liquid and solid phase chemical detectors via increased probability of detection and decreased limit of detection. The method can include using a swab collection substrate that increases the sensitivity of the detector by several orders of magnitude when swabbed from operationally relevant surfaces. For example, the target analyte can be obtained from a surface using an absorbent collection substrate that reduces or removes backgrounds interference. The collected analyte can be analyzed directly on the collection substrate using primarily a non-destructive spectroscopic technique such as Raman or FTIR, secondarily by solvent extraction from the collection substrate, or thirdly by thermal desorption from the collection substrate. Reach back analytical laboratory support is facilitated by the preservation of the target analyte in the vial for further analysis with portable or benchtop techniques such as ion mobility spectrometry, flame-spectrometry, high-performance liquid chromatography, gas chromatography, and/or mass spectrometry. The user can thus identify and mitigate the contact hazard in a much more rapid and sensitive manner then previously possible while still retaining the analyte for additional testing.

A system for analyzing a sample using spectroscopy, the system comprising: (i) a spectroscope; (ii) a sample vial comprising a swab removably sealable within an enclosure, the enclosure comprising at least one transparent portion to allow transmission of electromagnetic radiation; and (iii) a sample vial adaptor configured to affix to the spectroscope, and further comprising a sample vial receptacle configured to receive the sample vial, where the adaptor is configured to position the sample vial such that the transparent portion of the enclosure is between the swab and a laser of the spectroscope, and such that the swab is positioned at the focal distance of the laser.

According to an embodiment, the sample vial adaptor is configured to reversibly affix to the spectroscope.

According to an embodiment, the spectroscope includes a sample chamber, and where the sample vial adaptor is configured to insert into the sample chamber of the spectroscope.

According to an embodiment, where the sample vial further comprises a removable cap with a stem extending outwardly, the stem comprising the swab at the end distal to the cap, and further wherein the stem is suspended in the sample vial when the cap is affixed to the sample vial.

According to an embodiment, the stem includes an angle at the distal end to position the swab at an approximately 20 degree angle compared to the end of the stem proximal the cap.

According to an embodiment, the swab comprises an absorbent collection substrate.

According to an embodiment, wherein the sample vial includes a positioning tab, and wherein the sample vial receptacle comprises a positioning slot complementary to the positioning tab of the sample vial.

According to an embodiment, wherein the sample vial adaptor further comprises a probe receptacle configured to receive a probe of Raman instrument.

According to an aspect is a method for analyzing a sample using spectroscopy, the method comprising the steps of: (i) providing a transparent sample vial, the sample vial comprising a collection substrate; (ii) swabbing the collection substrate on a surface to be sampled; (iii) inserting the collection substrate within the sample vial such that the collection substrate is suspended within the sample vial; (iv) placing the sample vial in a sample vial receptacle of a sample vial adaptor, wherein the adaptor is affixed to the spectroscope and is configured to position the sample vial such that the swab is positioned at the focal distance of a laser of the spectroscope; and (v) analyzing the collection substrate using the spectroscope.

According to an embodiment, the adaptor comprises a mounting post configured to insert into a sample chamber of a spectroscope.

According to an embodiment, the sample vial comprises a swab removably sealable within an enclosure, the enclosure comprising at least one transparent portion to allow transmission of radiation.

According to an embodiment, the sample vial further comprises a removable cap with a stem extending outwardly, the stem comprising the swab at the end distal to the cap, and further wherein the stem is vertically suspended in the sample vial when the cap is affixed to the sample vial.

According to an aspect is a device for swabbing a surface, the device comprising: (i) an enclosure, wherein at least a portion of the enclosure is transparent; (ii) a cap configured to removably affix to the transparent enclosure; and (iii) a stem extending outwardly from the cap, the stem comprising a collection substrate at the end distal to the cap, and further comprising an angle at the distal end to position the collection substrate at an angle compared to the end of the stem proximal the cap; wherein the stem is suspended in the sample vial when the cap is affixed to the transparent enclosure.

According to an embodiment, the collection substrate comprises quartz fiber.

According to an aspect is a sample vial adaptor, the adaptor comprising a sample vial receptacle configured to receive a sample vial comprising a swab removably sealable within an at least partially transparent enclosure, wherein the sample vial adaptor is configured to affix to a spectroscope, and further wherein the sample vial adaptor is configured to position the sample vial such that the transparent portion of the enclosure is positioned between the swab and a laser of the spectroscope, and such that the swab is positioned at the focal distance of the laser.

According to an aspect is a system for analyzing a sample using spectroscopy, the system comprising (i) a spectroscope; (ii) a sample collector comprising a swab at a distal end of a stem; and (iii) a sample collector adaptor configured to affix to the spectroscope and including a sample collector receptacle configured to receive the sample collector, where the adaptor is configured to position the swab of the sample collector at the focal distance of the laser.

According to another aspect is a sample collector adaptor including a sample collector receptacle configured to receive a sample collector comprising a swab, the sample collector adaptor configured to affix to a spectroscope, and further where the sample collector adaptor is configured to position the sample collector such that the swab is positioned at the focal distance of the laser.

BRIEF DESCRIPTION OF THE DRAWINGS

The present invention will be more fully understood and appreciated by reading the following Detailed Description in conjunction with the accompanying drawings, in which.

DETAILED DESCRIPTION

According to an embodiment is a device, method, and system for sampling and analyzing sampled analyte from a surface for the presence of one or more chemical and/or biological agents in the field. The invention comprises a system for analyzing an acquired target analyte using Raman spectroscopy or another analytical device. According to an embodiment, the system includes a Raman spectroscope configured to obtain Raman spectral data from a target analyte, a sample swab used to obtain the analyte, and an adaptor which properly positions the sample swab, and such that the sample swab is positioned at the focal distance of the laser, and the swab substrate is positioned such that the laser is incident on the portion of the substrate containing the sample. Alternatively, the adaptor could be configured to eliminate the need for a vial making the adaptor the enclosure. For use with instruments that employ a fixed laser aperture (i.e., that do not feature a movable probe) and that therefore do not have a sample chamber, the sample vial adaptor may affix to the body of the device in such a way as to position the sample vial such that the swab is positioned at the focal distance of the laser, and the swab substrate is positioned such that the laser is incident on the portion of the substrate containing the sample.

Figure 1:
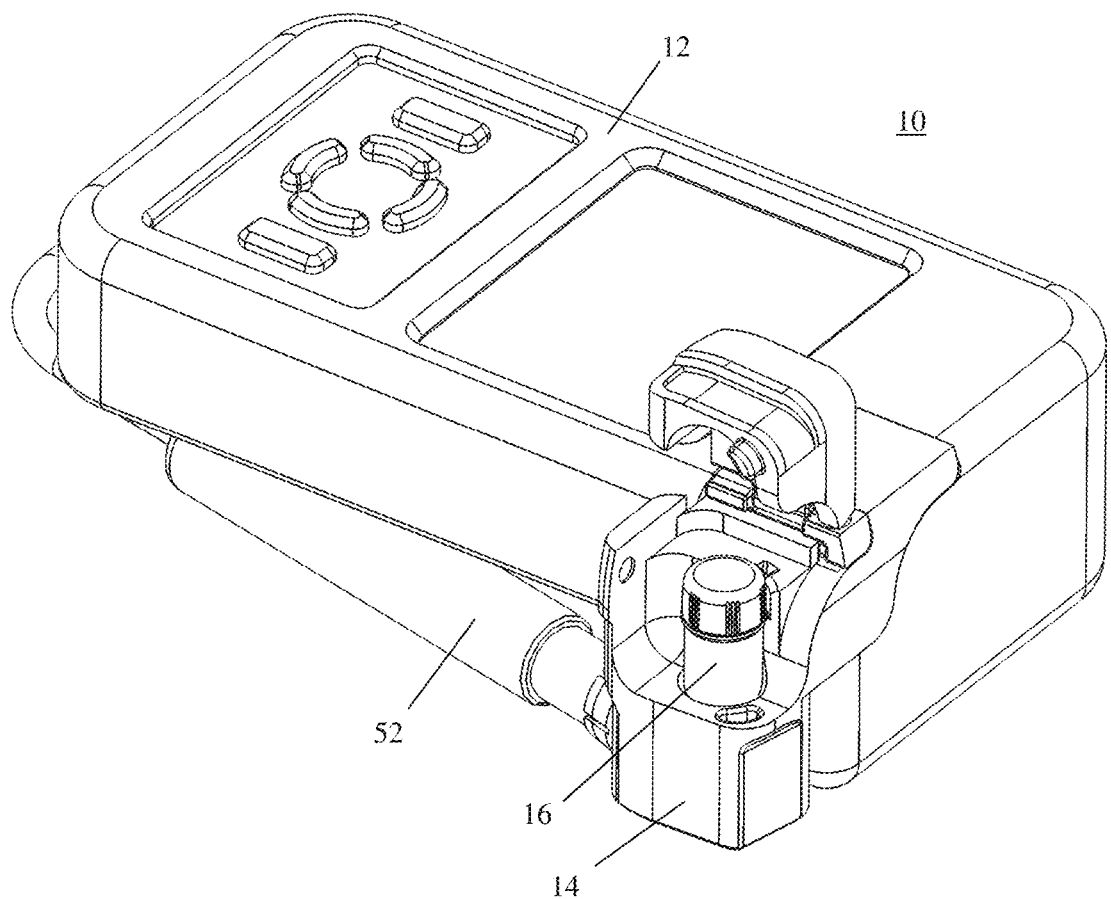
FIG. 1 is a schematic of a system for analyzing a sample using an analytical device in accordance with an embodiment.

Referring now to FIG. 1, a schematic of a system 10 for analyzing a sample using Raman spectroscopy is provided. According to an embodiment, the system includes a Raman spectroscope 12 configured to obtain Raman spectral data from a sample. Raman spectroscope 12 can be any commercial spectroscope, or can be a device designed and manufactured specifically for the system. The system further includes a sample swab 16 which is used to obtain the target analyte—potentially containing a chemical and/or biological agent or target analyte—for Raman spectroscopy. The sample swab fits into a sample vial which includes at least one transparent portion that allows the transmission of the laser from the spectroscope to the sample within the vial. According to an embodiment, Raman spectroscope 12 comprises an adaptor 14 which properly positions the sample vial such that the transparent portion of the enclosure is between the laser and the sample swab, and such that the sample swab is positioned at the focal distance of the laser.

Figure 2:
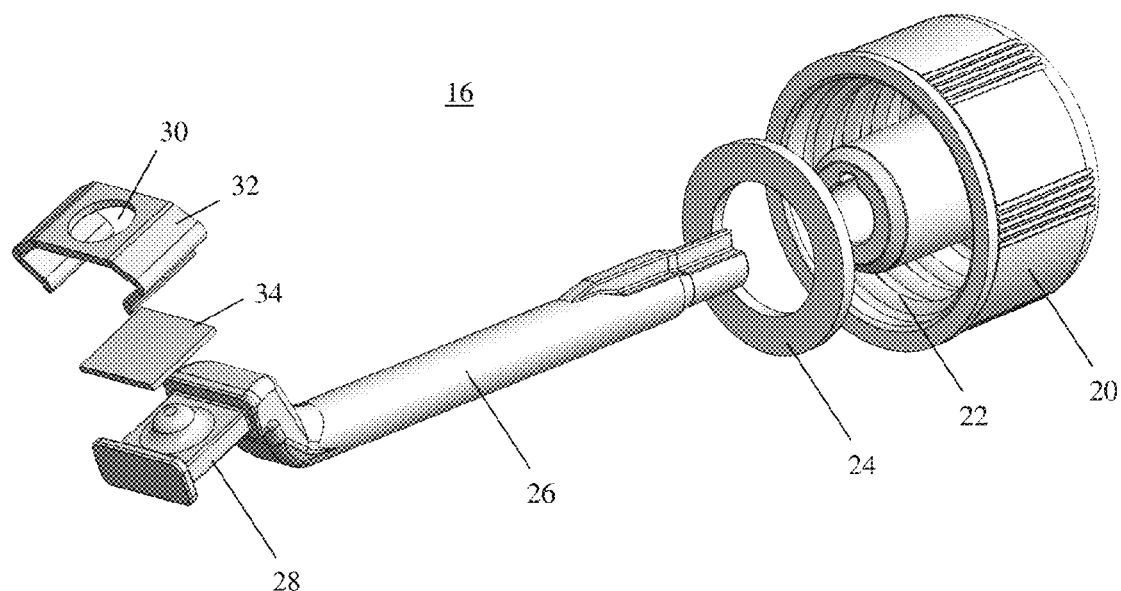
FIG. 2 is an exploded view of a sample swab in accordance with an embodiment.

Referring now to FIG. 2, an exploded view of a sample swab 16 in accordance with an embodiment is provided. According to an embodiment, sample swab 16 includes a cap 20 permanently or reversibly connected to stem 26. The cap can be made of any suitable material, including metal, plastic, or other polymers. According to one embodiment, the cap comprises polyether ether ketone ("PEEK") thermoplastic polymer and is manufactured using an injection molding process, although many other materials and manufacturing processes are possible. For example, the manufacturing process used to attach the cap to the stem could be either by a friction/snap fit, heat-staking, ultrasonic welding, or adhesive. Alternatively, the cap-stem assembly could be a single metal or plastic piece and not require joining. As shown in FIG. 2, cap 20 includes threads 22 which are used to fasten the cap to a sample vial 36 (shown in FIG. 4). Cap 20 can also include a cap liner 24, among other variations. Cap liner 24 facilitates the formation of a seal between the cap and sample vial 36, thereby sealing the sample and any targets or agents found in the sample within the enclosure. This allows for portability of the sample and thus safe transport to permit additional analyses either on site or in a laboratory. According to an embodiment, cap liner 24 can be made of a rubber or polymer that provides for tight sealing. For example, cap liner 24 can be made of a synthetic rubber such as a chemically resistant fluoroelastomer, which provides a seal and prevents degradation by chemicals that could potentially be found within samples. Many other types of compounds are possible.

Figure 3:
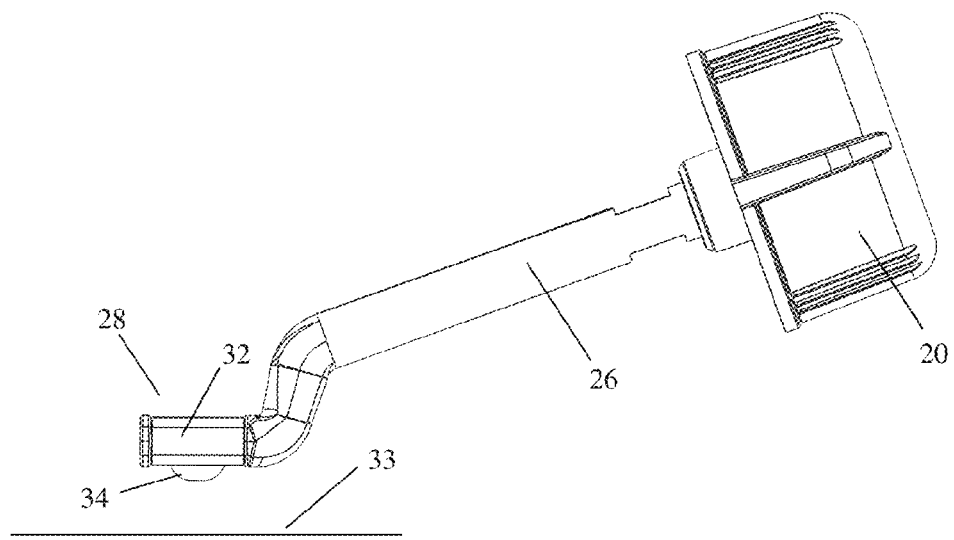
FIG. 3 is a side view of an assembled sample swab in accordance with an embodiment.

Stem 26 of sample swab 16 is positioned approximately coaxially to the threads of cap 20. The stem can be made of one or more of a variety of materials, including but not limited to metal, plastic, or a polymer. For example, according to one embodiment the stem is composed of an aluminum or aluminum alloy. The stem can be manufactured using an injection molding process, or can be stamped, punched, or cast, among other manufacturing methods. The stem can be permanently or reversibly affixed to the cap 20, or the cap and stem can be manufactured together as a single piece or component. As one example, the stem can be bonded to the cap using a high-strength adhesive, or the two components can be heat-staked together, among other methods. At the distal end of the stem is the swabbing portion 28. According to an embodiment, swabbing portion 28 comprises a sample substrate 34 and a clip 32. The clip, which can be metal, plastic, and/or another material, has arms that are crimped over or around the substrate and around a portion of the distal end in order to fasten the substrate in place. In the embodiment depicted in FIG. 2, the clip has a hole 30 which allows the substrate to interact with the surface, as shown in FIG. 3. As an example, the clip can be punched from an aluminum sheet and can be pre-bent to facilitate crimping or bending over the substrate. According to another embodiment, the swab can include only the substrate without the clip.

Substrate 34 can be any substrate capable of gathering a sample from a surface. Preferably, the substrate is inert to avoid interacting with the target analyte and potentially leading to degradation. Also, the substrate should be designed or selected to avoid interfering with the Raman spectroscopy or other analysis, which would lead to decreased sensitivity. Note, however, that there may be applications where the target analyte is intentionally modified by the substrate for analysis, in which case substrate 34 is intentionally not inert but is instead designed to modify the target analyte when the substrate and target analyte come into contact. For example, the substrate could be integrated or functionalized with bio-receptors (e.g. biomarkers, antibodies or molecular conjugates, DNA/RNA-based taggants and probes, or PCR products) which when activated are directly or indirectly detectable by Raman spectroscopy or other analytical techniques. According to one embodiment, the collection substrate is composed of, or comprises, one or multiple features that include materials that are derivative of oxides of metaloids, or metals. Appropriate collection substrate could be a porous, fibrous material such as those typically used in filters, woven fabrics, or felts. Polymeric membranes, such as cellulose, or those composed of organic binders and inorganic woven fibers, may also be suitable in some cases. As just one example, quartz fibers can be particularly well-suited for low level target analyte acquisition. In addition, nonpermeable collection substrate surfaces modified in either a heterogeneous or homogeneous manner may be suitable. This could be homogeneous metal or alloy with or without uniform repeating chemical functionalization. In addition, the substrate can include surface enhanced Raman spectroscopy ("SERS")-active materials to allow SERS analysis, thereby potentially achieving even lower levels of detection without interfering with the target analyte or agent of interest. Alternatively, a suitable heterogeneous material with SERS or surface enhanced resonance Raman scattering ("SERRS") attributes such as metallic nanoparticle decorated filter paper, membrane, or sol-gel is feasible. Alternatively, homogeneous, nanostructured, or uniformly functionalized substrates are possible to attain an amplified spectroscopic signal.

As shown in FIG. 3, the assembled sample swab 16 is structured such that the stem 26 is angled with respect to the swabbing portion 28. For example, the stem can include an angled feature at its distal end which positions the substrate at an angle compared to the end of the stem proximal the cap. A suitable angle might be, for example, approximately 20 degrees, although a wide range of angles are possible. This allows the user to hold the swab by the cap at an angle convenient for swabbing a surface 33 with substrate 34. This also positions the substrate 34 at an optimized location and angle within the sample vial for analysis by the Raman spectroscope or other analytical devices.

Figure 4:
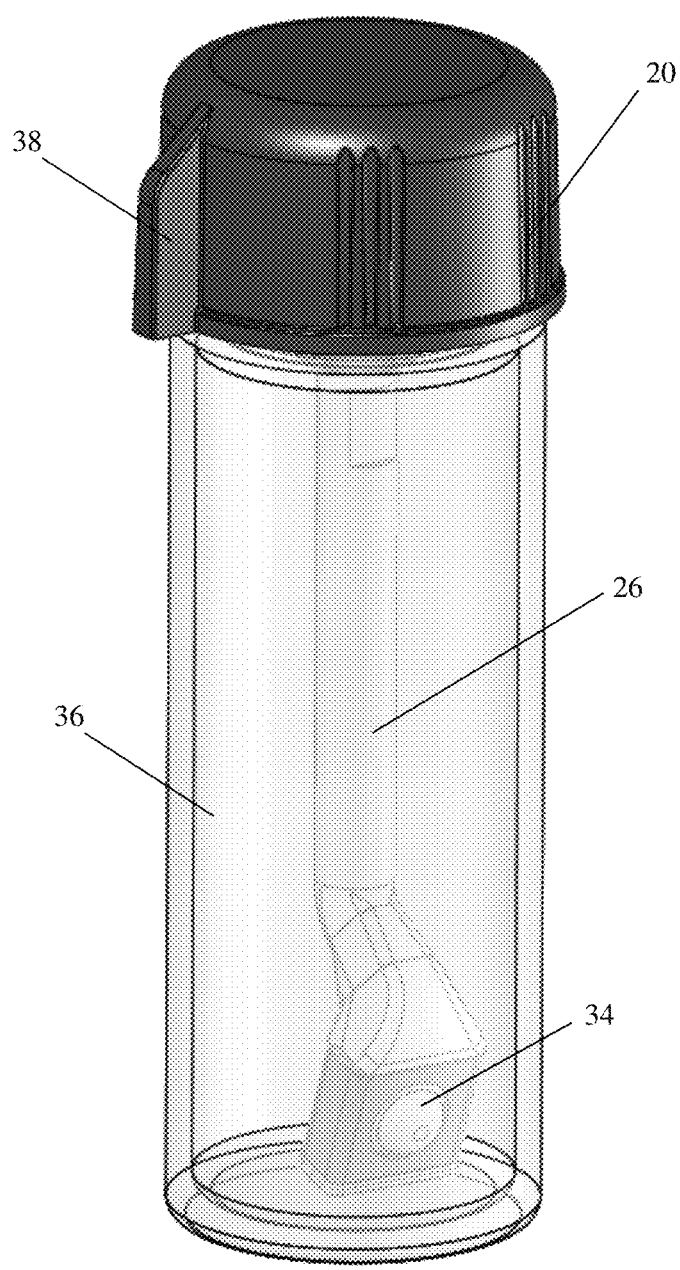
FIG. 4 is a side view of an assembled sample swab sealed within a sample vial in accordance with an embodiment.

Referring now to FIG. 4, a side view of a sample vial 36 containing a sample swab 16 is provided. The sample swab is any of the embodiments described or otherwise envisioned herein. The sample vial, in this embodiment, is a glass or plastic enclosure for the sample swab. This allows the radiation from the Raman spectroscope to reach the substrate. The sample vial can include threads (not shown) that are complementary to threads 22 of the cap, thereby providing a sealing mechanism for the cap and the vial. For example, in the embodiment shown in FIG. 4, the cap has been threaded onto sample vial 36 to form a seal. According to an embodiment, the cap includes a tab 38 or other positioning means which is utilized along with a receptacle (see item 40 of FIG. 5, for example) in order to properly position the substrate 34 in the direction of the Raman laser or other analysis instrument. Since the cap and stem are directly connected, the proper positioning of the cap dictates the proper positioning of the stem and the substrate. In this example the sample vial is a transparent glass or plastic enclosure, and thus the radiation from the Raman spectroscope can penetrate the enclosure and interact with the substrate regardless of which portion of the enclosure the substrate ultimately faces. In an embodiment where the enclosure is only partially transparent, such as a sample vial with just a transparent window or wall, proper alignment will require the proper positioning of both the substrate and the window or wall. When the cap is affixed to the vial, the stem and collection substrate are vertically suspended in the sample vial without touching any surface.

Figure 5:
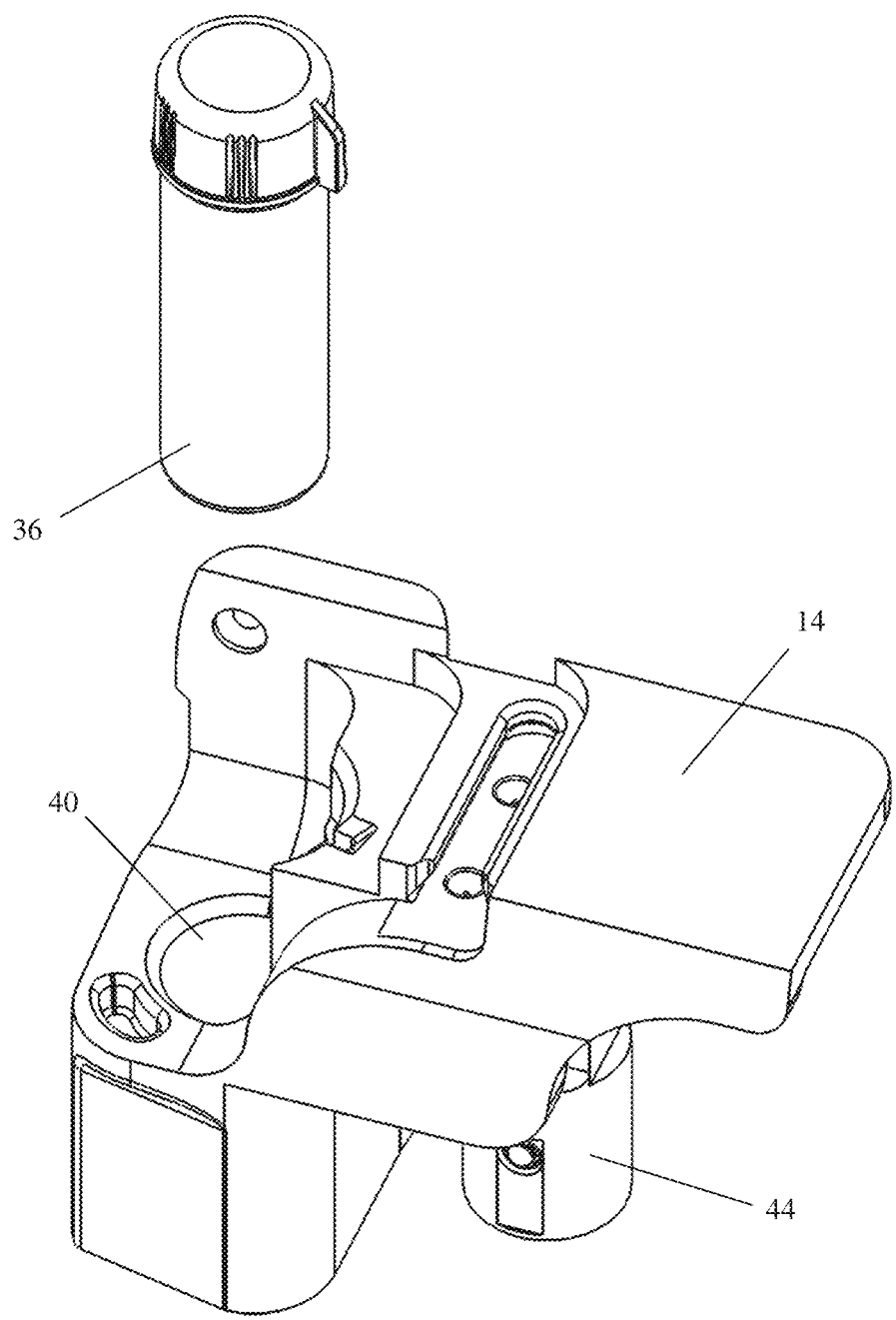
FIG. 5 is a perspective view of a sample vial and adaptor in accordance with an embodiment.
Figure 6:
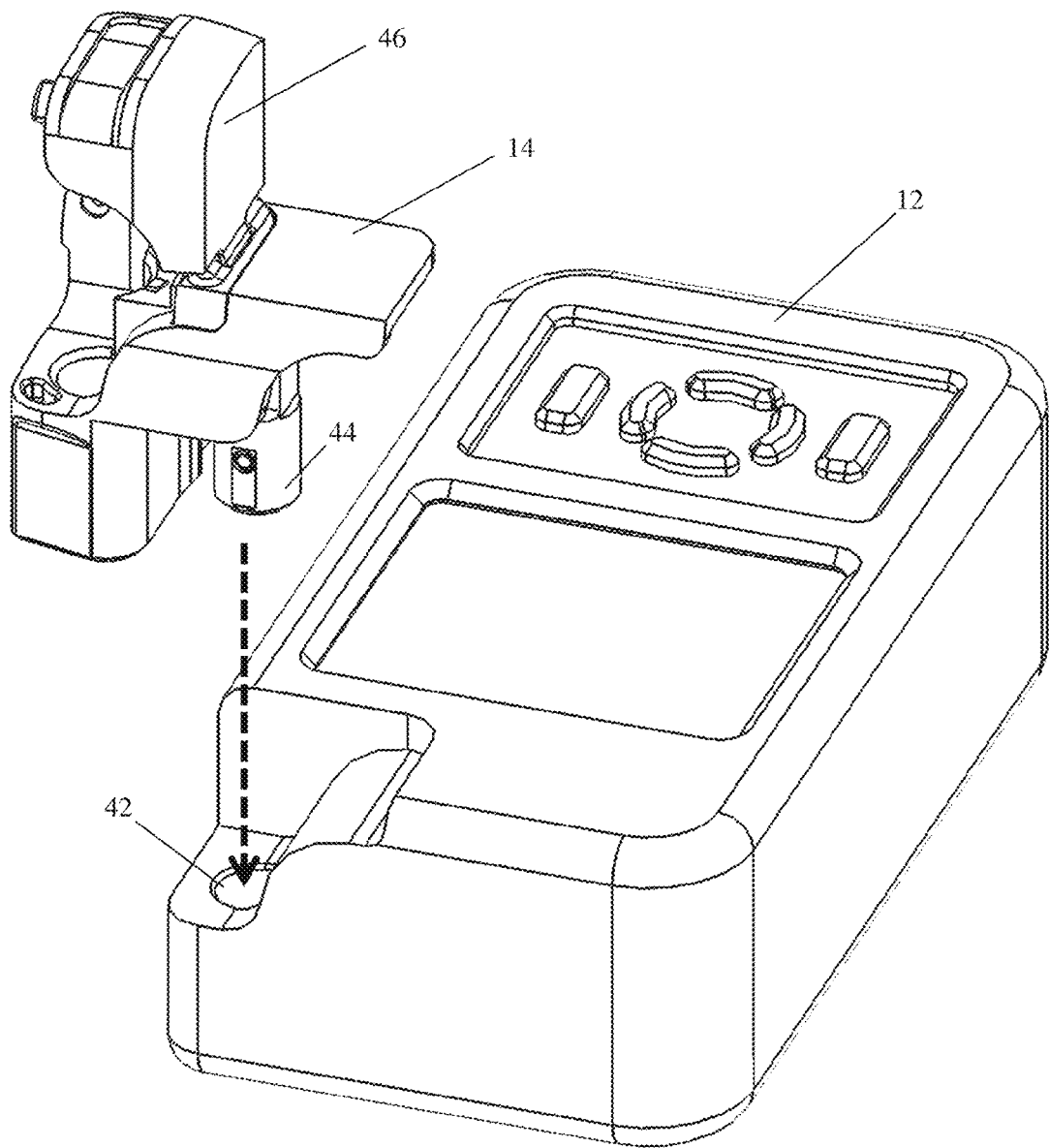
FIG. 6 is a perspective view of an adaptor and an analytical device in accordance with an embodiment.

Referring now to FIG. 5, a schematic of an adaptor 14 and sample vial 36 is provided. According to an embodiment, the adaptor is configured to properly position the sample vial 36 within a sample vial receptacle 40 such that a transparent portion of the sample vial is between the laser and the collection substrate of the sample swab, and such that the collection substrate is positioned at the focal distance of the laser. As shown in FIG. 6, Raman spectroscope 12 includes a sample vial chamber 42 that normally receives the stock sample vial sold for that spectroscope. However, in order to improve sensitivity of the Raman spectroscope, adaptor 14 is utilized with sample vial 36. Accordingly, the adaptor can include, for example, a mounting post 44 that affixes the adaptor to the device and fits tightly within sample chamber 42 of Raman spectroscope 12. The adaptor can also include a lid 46 that fits over the sample vial receptacle 40. Lid 46 can snap, click, or otherwise lock or fasten in place, for example.

Figure 7:
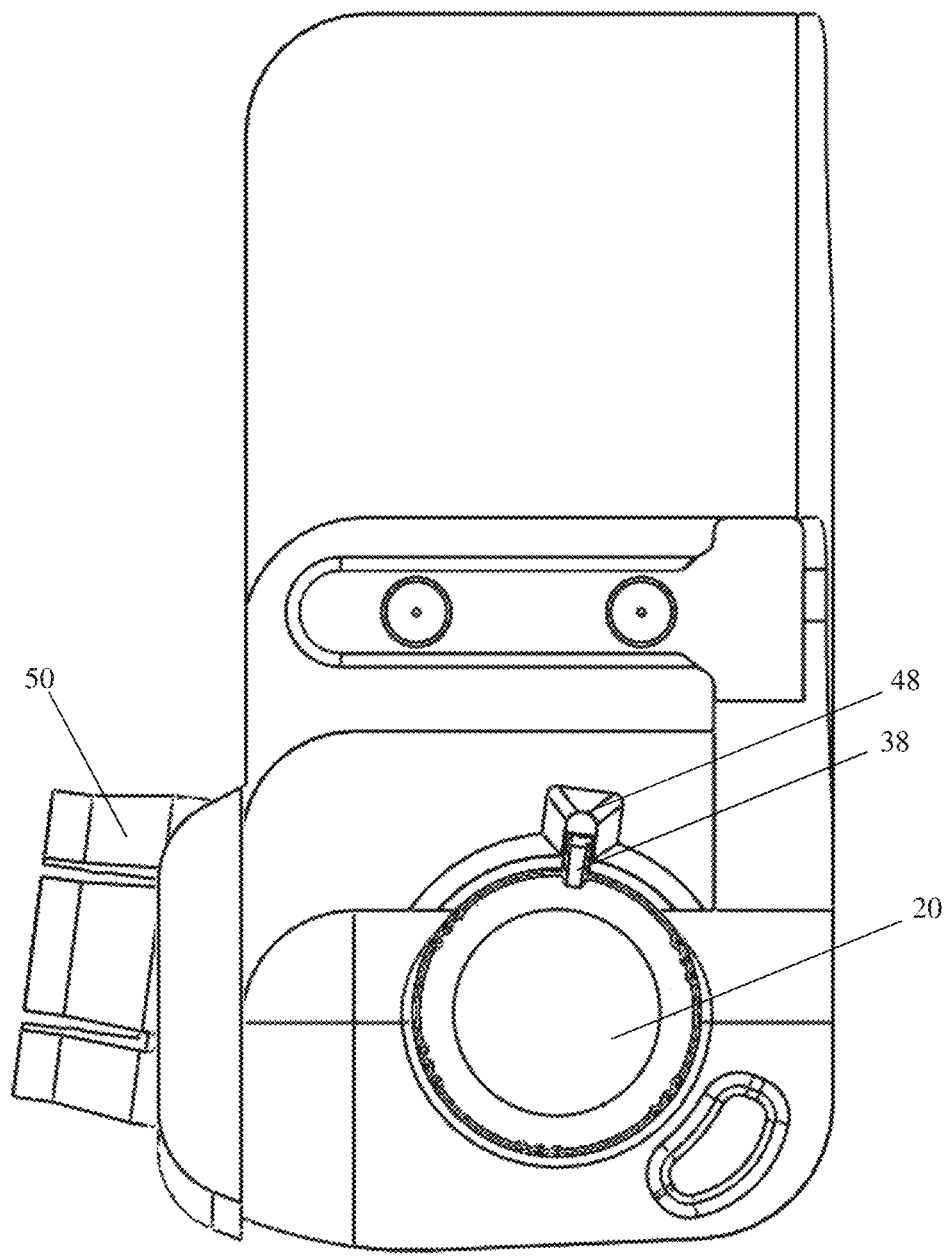
FIG. 7 is a top view of a sample vial inserted into an adaptor in accordance with an embodiment.

As shown in FIG. 7, the adaptor can also include a slot 48 into which tab 38 of cap 20 fits, such that the sample vial will only slide completely into the sample vial receptacle 40 if the tab 38 of the cap is properly aligned with the slot 48 to allow the tab to slide into the slot. If the adaptor includes a lid 46, the lid will only properly close if the sample vial receptacle 40 is properly aligned by aligning the tab and slot.

Figure 8:
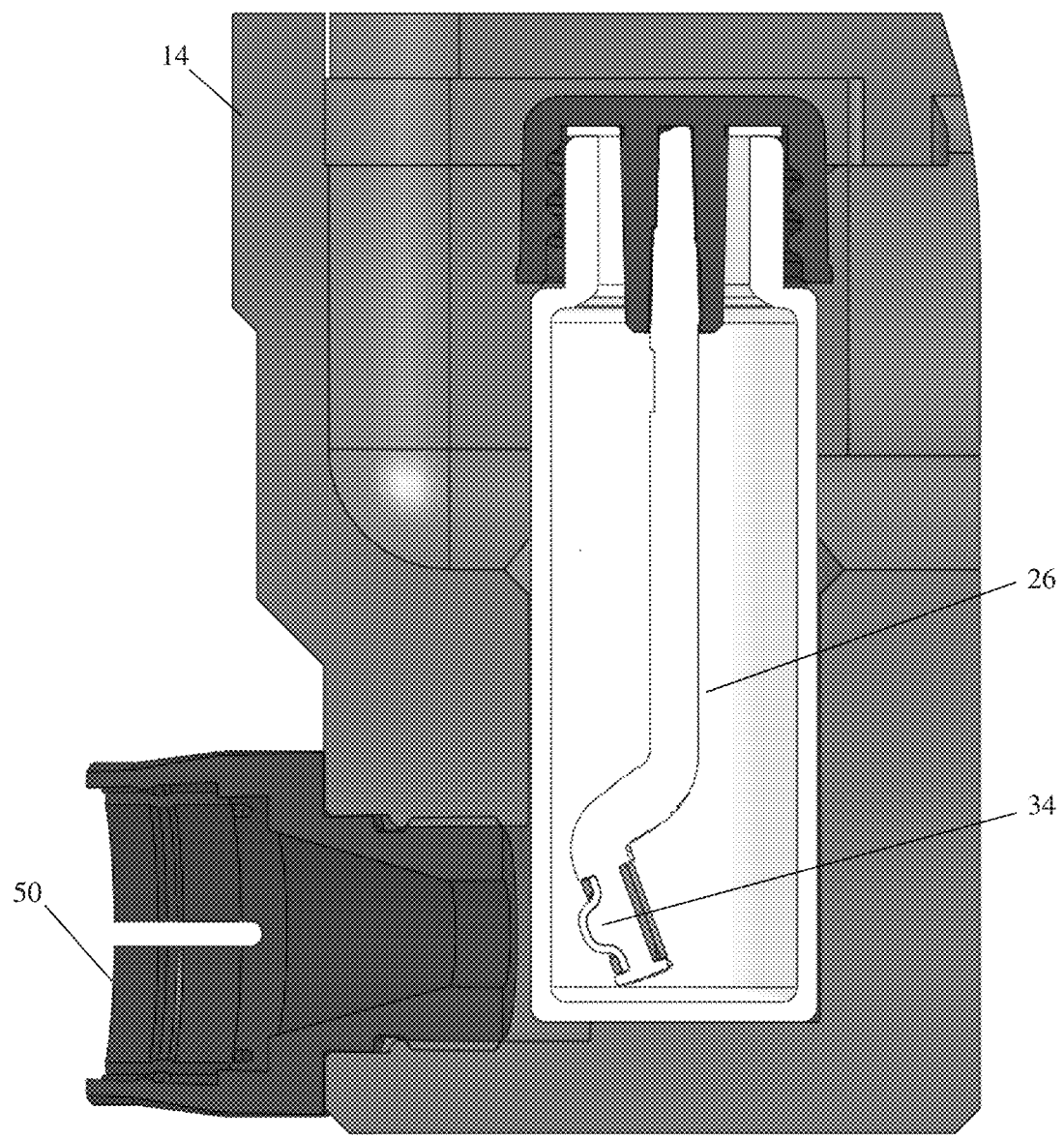
FIG. 8 is a side cutaway view of a sample vial inserted into an adaptor in accordance with an embodiment.

Also shown in FIG. 7, the adaptor can include a probe receptacle 50 for the probe 52 of the Raman spectroscope 12. During operation, probe 52 adds flexibility to the Raman spectroscope 12, allowing a wider variety of surfaces to be analyzed. According to an embodiment of the system described or otherwise envisioned herein, the probe tip is inserted into the probe receptacle 50 of the adaptor 14, as shown in FIG. 1. This brings the probe tip and the substrate 34 into close, properly aligned orientation, as shown in FIG. 8, in which the sample vial is fully inserted into sample vial receptacle 40. Once the probe tip and substrate 34 are so aligned, the user can obtain Raman spectra using the system.

In addition to other benefits and improvements described herein and/or inherent to the system, the sample vial 36 seals the collection substrate and sample—which may contain one or more chemical and/or biological agents or targets—within the vial, thereby preventing contamination of the probe 52 or Raman spectroscope 12. Further, the sample vial immobilizes the sample to allow for stable repetitive interrogation of the substrate, thereby providing accumulation of spectral data.

Figure 9:
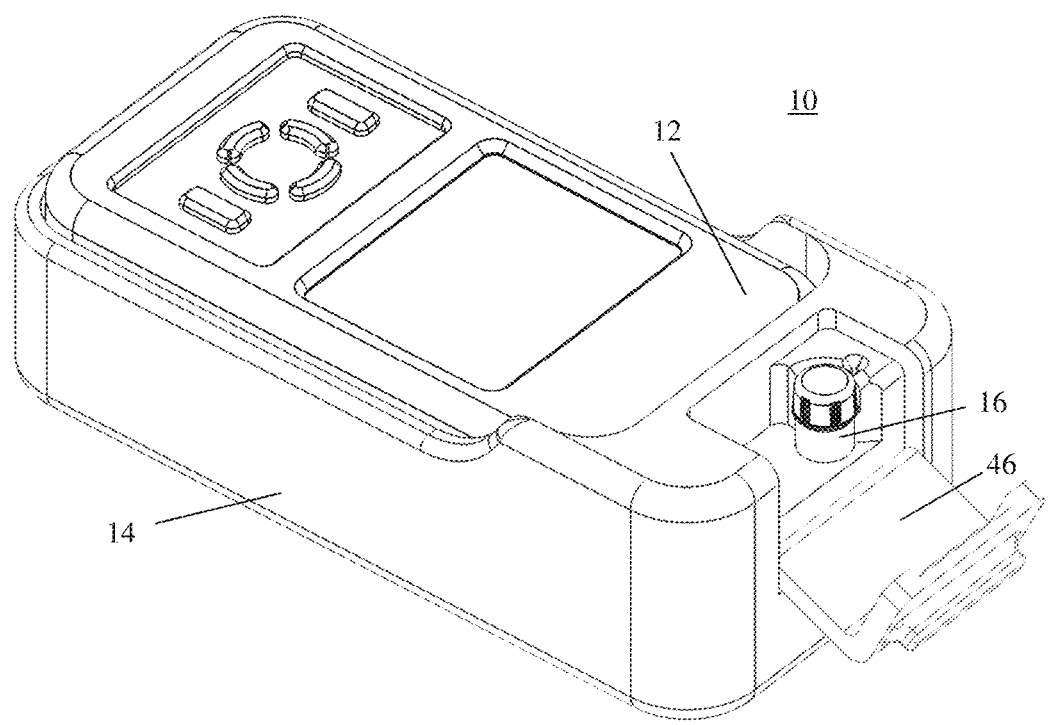
FIG. 9 is a schematic of a system for analyzing a sample using an analytical device in accordance with an embodiment.
Figure 10:
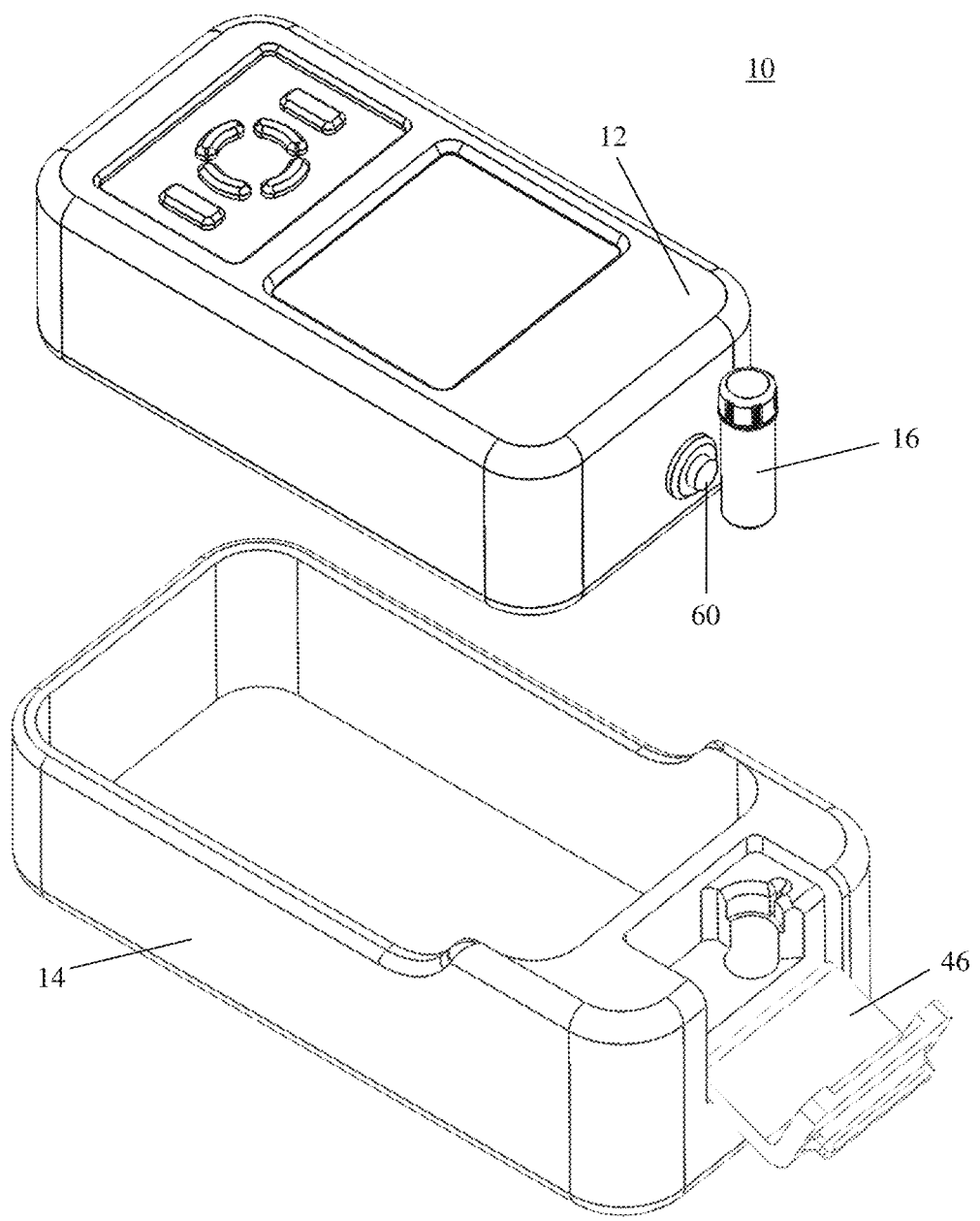
FIG. 10 is an exploded view of the system of FIG. 9, in accordance with an embodiment.

Many other embodiments of a system for analyzing a target analyte on a sample swab using Raman spectroscopy are possible. Referring to FIGS. 9 and 10, in one embodiment, is such a system 10. The system comprises a Raman spectroscope 12 configured to obtain Raman spectral data from a sample. Raman spectroscope 12 can be any commercial spectroscope, or can be a device designed and manufactured specifically for the system. The system further includes a sample swab 16 which is used to obtain the target analyte—potentially containing a chemical and/or biological agent or target analyte—for Raman spectroscopy. According to an embodiment, Raman spectroscope 12 lacks a probe 52, instead comprising a laser outlet 60 (shown in FIG. 10). In order to properly position the sample swab, system 10 includes an adaptor 14 that functions as a housing to position the spectroscope 12 and the sample swab 16, as shown in FIG. 9. Adaptor 14 also optionally includes a lid 46.

Figure 11:
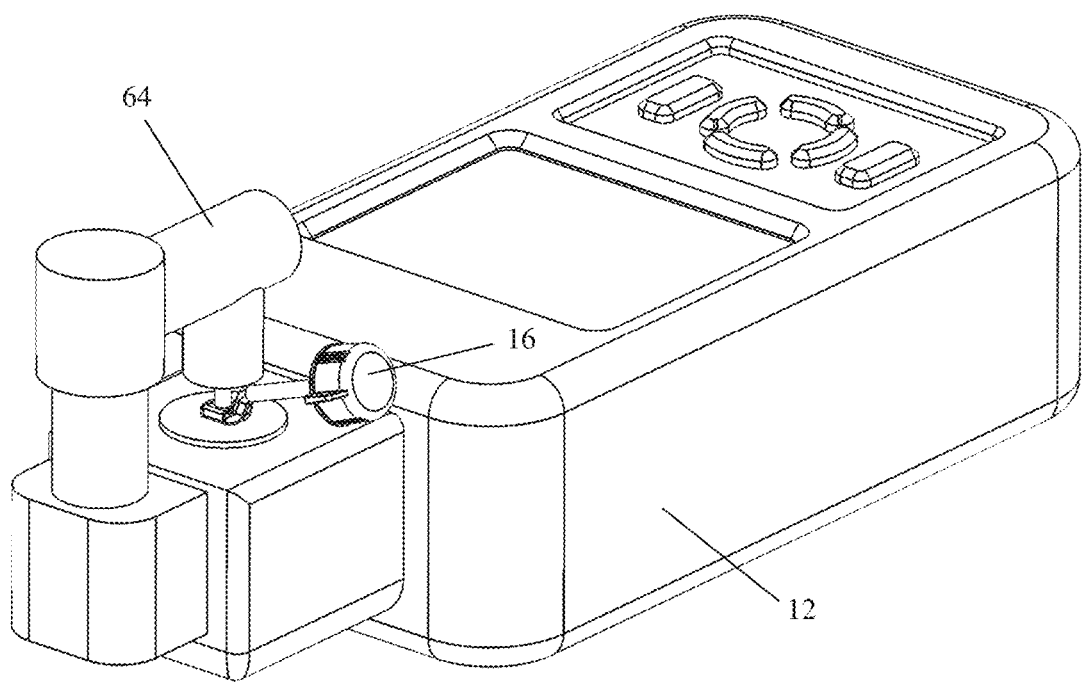
FIG. 11 is a schematic of a system for analyzing a sample using an analytical device in accordance with an embodiment.

Referring to FIG. 11 is a system 10 for analyzing a target analyte on a sample swab using a Fourier transform infrared spectroscope ("FTIR") 12. Spectroscope 12 can be a commercial spectroscope, or can be a device designed and manufactured specifically for the system. For example, spectroscope 12 can be an attenuated total reflectance ("ATR") FTIR. System 10 further includes a sample swab 16 which is used to obtain the target analyte. According to an embodiment, spectroscope 12 includes a sampling anvil 64 under which the sample swab 16 is positioned for analysis.

Method of Analysis

Figure 12:
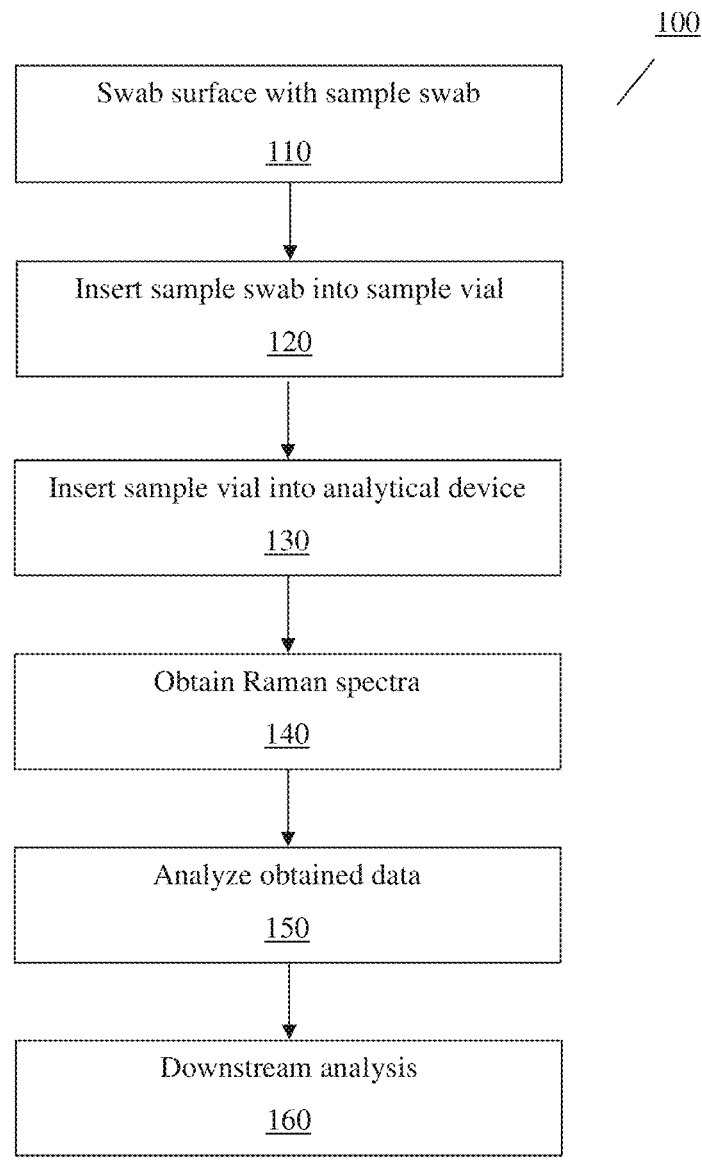
FIG. 12 is a flowchart schematic of a method for analyzing a sample in accordance with an embodiment.

Referring now to FIG. 12, a method 100 for investigating a sample is provided. At step 110, a sample swab 16 is used to swab a surface. Sample swab 16 can be any of the embodiments described and/or envisioned herein. For example, sample swab 16 can include a cap 20 permanently or reversibly connected to a stem 26, the step including a swabbing portion 28 with a sample substrate 34 and a clip 32. The stem 26 can be angled approximately 45 degrees to the swabbing portion 28 to allow the user to hold the swab by the cap at an angle convenient for swabbing a surface 33 with substrate 34. The surface to be swabbed can be any surface suspected or capable of hosting, having, or carrying a target analyte such as a chemical and/or biological agent of interest. For example, the surface can be skin, clothing, walls, objects, ground, and almost any other surface. The target analyte believed to be or possibly found on the surface can be a liquid target and/or a solid target.

At step 120, the sample swab 16 is carefully inserted into sample vial 36. According to a preferred method, the sample swab is inserted into the sample vial such that the collection substrate 34 does not touch any of the surfaces of the vial, thereby preventing contamination. If the cap 20 and sample vial 36 are threaded, the cap can be screwed onto the vial to seal the sample swab inside the vial. Otherwise, the sample swab and vial can be snapped or otherwise assembled. The sample vial 36 now contains the sample swab 16, possibly sealed if so configured, and the vial is now ready for analysis.

At step 130, the sample vial 36 is inserted into the analytical device, which can be any analytical device capable of analyzing the sample on the substrate through the sample vial. According to an embodiment, the analytical device is a Raman spectroscope 12. In some embodiments, the sample vial is inserted into the sample receptacle provided by the Raman spectroscope during manufacture. In other embodiments, in order to improve sensitivity, the sample vial is inserted into a sample receptacle 40 provided by an adaptor 14. The adaptor can be any of the adaptors described or otherwise envisioned herein. For example, the adaptor can include a mounting post 44 that fits tightly within sample chamber 42 of Raman spectroscope 12 to correctly position the adaptor, or could interface with the spectroscopic laser probe in other ways such as a clamp, screw on adapter, or clip. The adaptor may also include a lid 46 that encloses the sample, as well as a probe receptacle 50 for the probe 52 of the Raman spectroscope 12.

At step 140, Raman spectra are obtained using the Raman spectroscope 12, and at step 150 of the method in FIG. 12, the obtained data is analyzed to identify and/or otherwise characterize or quantitate any chemical and/or biological agents or targets on the substrate (and thus on the surface that was swabbed). If the analytical device is not a Raman spectroscope, step 140 can comprise obtaining the respective data for that analytical device and step 150 can comprise analyzing that obtained data to identify and/or otherwise characterize or quantitate the chemical and/or biological agents or targets. Analyzing Raman or other analytical data can be performed using, for example, known techniques in the art. According to an embodiment, the method increases the sensitivity of the detector by several orders of magnitude when swabbed from operationally relevant surfaces.

At step 160, the target analyte present on the collection substrate and encapsulated in the vial can be processed for downstream analysis. Since the sample is encapsulated, it can safely be transported to a supporting laboratory and analyzed by a secondary analytical device for higher fidelity and greater sensitivity than available in field detection platforms. For example, the target analyte could diluted with an appropriate aqueous or organic solvent, extracted from the collection substrate into the solvent, and analyzed using an analytical device via liquid chromatography, gas chromatography, ion mobility spectrometry, or mass spectrometry. Alternatively, the target analyte could be thermally desorbed from the collection substrate without the need for solvent and injected into the inlet of a spectrometer.

EXAMPLES

According to an embodiment, system 10 is used to detect and/or identify trace chemical and/or biological targets or agents present in a sample. Summaries of experiments using an experimental set-up of system 10 are shown Tables 1-5. In these experiments, the Raman spectroscope was a First-Defender™ RMX Raman Spectroscope (Thermo Scientific®) set to an excitation wavelength of 785 nm. The Raman spectroscope rapidly detected liquid challenges such as chemical warfare agent ("CWA") simulants, directly on the sample swab collection substrate at volumes of 100 nL (115 µg), in less than 10 seconds. On operational surfaces such as glass, metal, painted metal, plastic, Tychem® fabric, wallboard, and CARC, liquid droplets of 500 nL showed rapid detection with the assistance of a sample swab. The overall detection rate of liquid simulants increased by as much as 87% from the dataset presented below in Tables 2 & 3 by utilizing the sample swab. Even in the presence of interferents such as Aqueous Film-Forming Foam ("AFFF"), diesel fuel, and Arizona Road Dust ("ARD"), the detection rate increased to as much as 86% from the dataset presented below in Table 4. Dry solid challenges of explosive ingredient, ammonium nitrate achieved positive detections down to 5 µg and an increased detection rate up to 81% from the dataset shown below in Table 5.

TABLE 1

Summary of Surface Detection Capability of Liquids and Solids

| Phase | Range Tested | # of Trials | Est. LOD |
|---|---|---|---|
| Solids | 5-500 µg | 99 | ~5 µg |
| Liquids | 0.1-2 µL | 192 | <0.1 µL | where "Est. LOD" is the estimated limit of detection based on these experiments, although lower limits of detection may be possible with other agents and/or system modifications or set-ups.

Using the same set-up, neat chemical simulants and mixtures were tested against a number of surfaces as indicated in TABLES 2-5.

TABLE 2

Detection Rate of 0.5 µL Liquid Challenges of tributyl phosphate (TBP) and 60/40 (mol %) (TBP)/pinacolyl methylphosphonic acid ("PMPA")

| Surface | TBP Direct | TBP Swab | TBP PMPA Direct | TBP PMPA Swab |
|---|---|---|---|---|
| Glass | 0/3 | 3/3 | 0/3 | 3/3 |
| Stainless Steel | 2/3 | 3/3 | 0/3 | 1/3 |
| Painted Metal | 3/3 | 3/3 | 0/3 | 3/3 |
| CARC | 0/3 | 3/3 | 0/3 | 3/3 |
| TyChem CPF3 | 0/3 | 3/3 | 0/3 | 3/3 |
| DETECTION RATE | 5/15 (33.3%) | 15/15 (100%) | 0/15 (0%) | 13/15 (86.7%) |

Figure 13A:
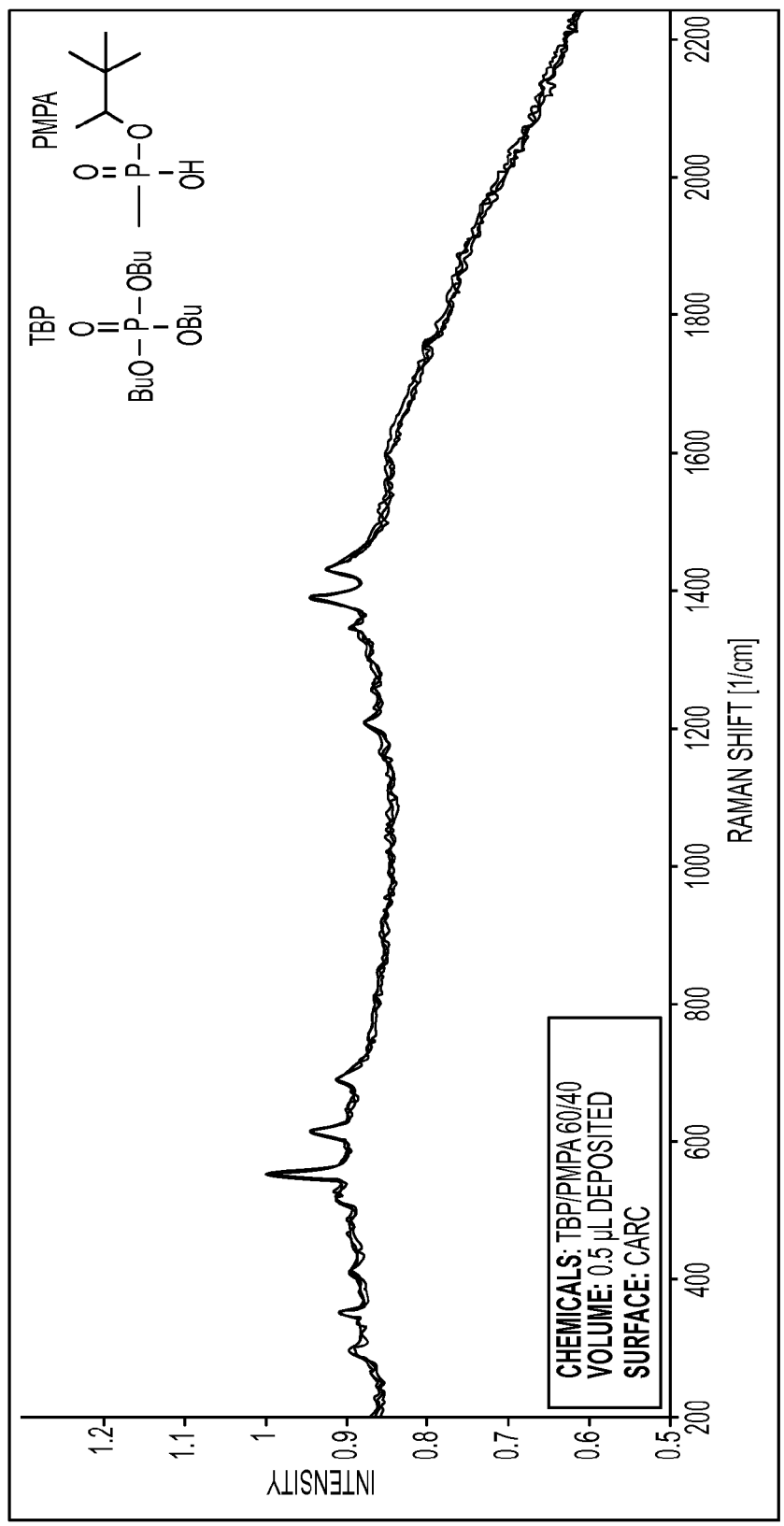
FIG. 13A is a graph of Raman spectral overlay of n=3 replicates of 0.5 µL liquid challenges of tributyl phosphate/pinacolyl methyl phosphonic acid (TBP/PMPA, 60/40 mol %) directly on Chemical Agent Resistant Coating ("CARC").
Figure 13B:
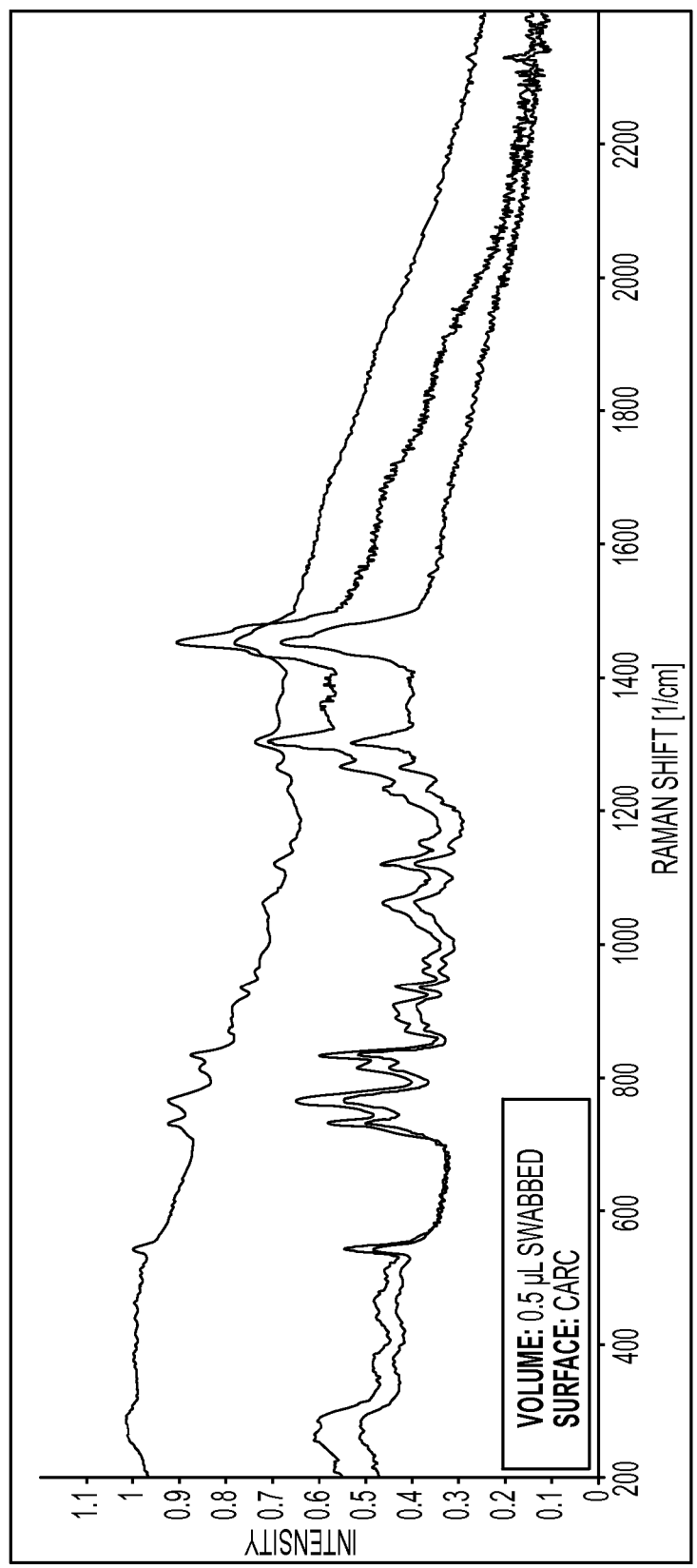
FIG. 13B is a graph of Raman spectral overlay of n=3 replicates of 0.5 µL liquid challenges of tributyl phosphate/pinacolyl methyl phosphonic acid (TBP/PMPA, 60/40 mol %) using a swab of CARC.

As shown in FIGS. 13A and 13B, the probability of detecting small amounts of a liquid chemical such as tributyl phosphate (TBP) directly on a surface that has an inherently strong background signal often obscures the signal attributed to the target analyte. Removing it from the surface by utilizing the swab system with an integral sample collection substrate free of spectroscopic interference eliminates the background signal from the collected spectra resulting in the detection rate when analyzed directly on CARC and when swabbed from CARC increasing from 0% (FIG. 13A) to 100% (FIG. 13B) respectively.

TABLE 3

Detection Rate of 0.5 µL Liquid Challenges of 2-Chloroethyl phenyl sulfide ("CEPS") and 60/40 (mol %) CEPS/Thiodiglycol ("TDG")

| Surface | CEPS Direct | CEPS Swab | CEPS TDG Direct | CEPS TDG Swab |
|---|---|---|---|---|
| Glass | 3/3 | 3/3 | 0/3 | 3/3 |
| Stainless Steel | 3/3 | 3/3 | 3/3 | 3/3 |
| Painted Metal | 3/3 | 3/3 | 3/3 | 3/3 |
| CARC | 0/3 | 3/3 | 0/3 | 3/3 |
| TyChem CPF3 | 0/3 | 3/3 | 3/3 | 3/3 |
| PMMA Plastic | 3/3 | 3/3 | 0/3 | 3/3 |
| Wallboard | 2/3 | 3/3 | 2/3 | 3/3 |
| DETECTION RATE | 14/21 (33.3%) | 21/21 (100%) | 11/21 (52.4%) | 21/21 (100%) |

TABLE 4

Detection Rate of 0.5 µL Liquid Challenges of TBP with Interferents

| Surface | TBP AFFF Direct | TBP AFFF Swab | TBP Diesel Direct | TBP Diesel Swab | TBP ARD Direct | TBP ARD Swab |
|---|---|---|---|---|---|---|
| Glass | 0/3 | 3/3 | 0/3 | 3/3 | 0/3 | 1/3 |
| Stainless Steel | 0/3 | 0/3 | 0/3 | 2/3 | 0/3 | 3/3 |
| Painted Metal | 2/3 | 0/3 | 1/3 | 3/3 | 0/3 | 0/3 |
| CARC | 0/3 | 3/3 | 0/3 | 3/3 | 0/3 | 1/3 |
| TyChem CPF3 | 0/3 | 2/3 | 0/3 | 3/3 | 0/3 | 3/3 |
| PMMA Plastic | 0/3 | 2/3 | 0/3 | 1/3 | 0/3 | 1/3 |
| Wallboard | 0/3 | 3/3 | 0/3 | 3/3 | 0/3 | 2/3 |
| DETECTION RATE | 2/21 (9.5%) | 13/21 (61.9%) | 1/21 (4.8%) | 18/21 (85.7%) | 0/21 (0%) | 11/21 (52.3%) |

TABLE 5

Detection Rate of Ammonium Nitrate ("AN") Solid Challenges of 5.5 and 55 µg

| | <5.5 µg (dry sampling) | | 55 µg (moistened swab) | |
|---|---|---|---|---|
| Surface | AN Direct | AN Swab | AN Direct | AN Swab |
| Glass | 0/3 | 3/3 | 0/3 | 3/3 |
| Stainless Steel | 0/3 | 1/3 | 1/3 | 3/3 |
| Painted Metal | 1/3 | 2/3 | 0/3 | 2/3 |
| CARC | 0/3 | 1/3 | 0/3 | 3/3 |
| TyChem CPF3 | No data | No data | 0/3 | 3/3 |
| PMMA Plastic | 0/3 | 2/3 | 1/3 | 2/3 |
| Wallboard | No data | No data | 0/3 | 3/3 |
| DETECTION RATE | 1/15 (6.7%) | 9/15 (60.0%) | 1/21 (4.8%) | 18/21 (85.7%) |

Figure 14A:
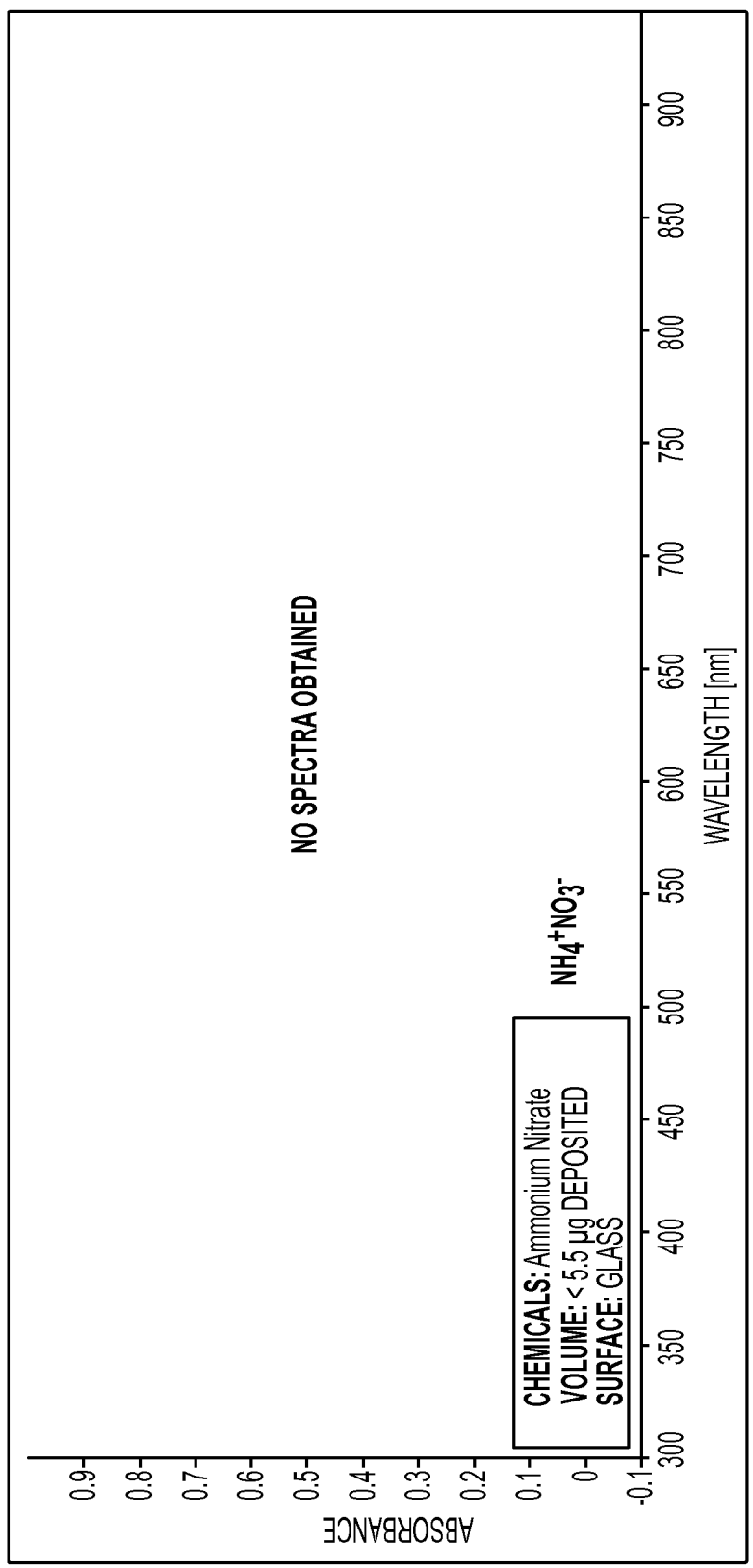
FIG. 14A is a graph of Raman spectral overlay of n=3 replicates of <5 µg solid ammonium nitrate challenges directly on glass.
Figure 14B:
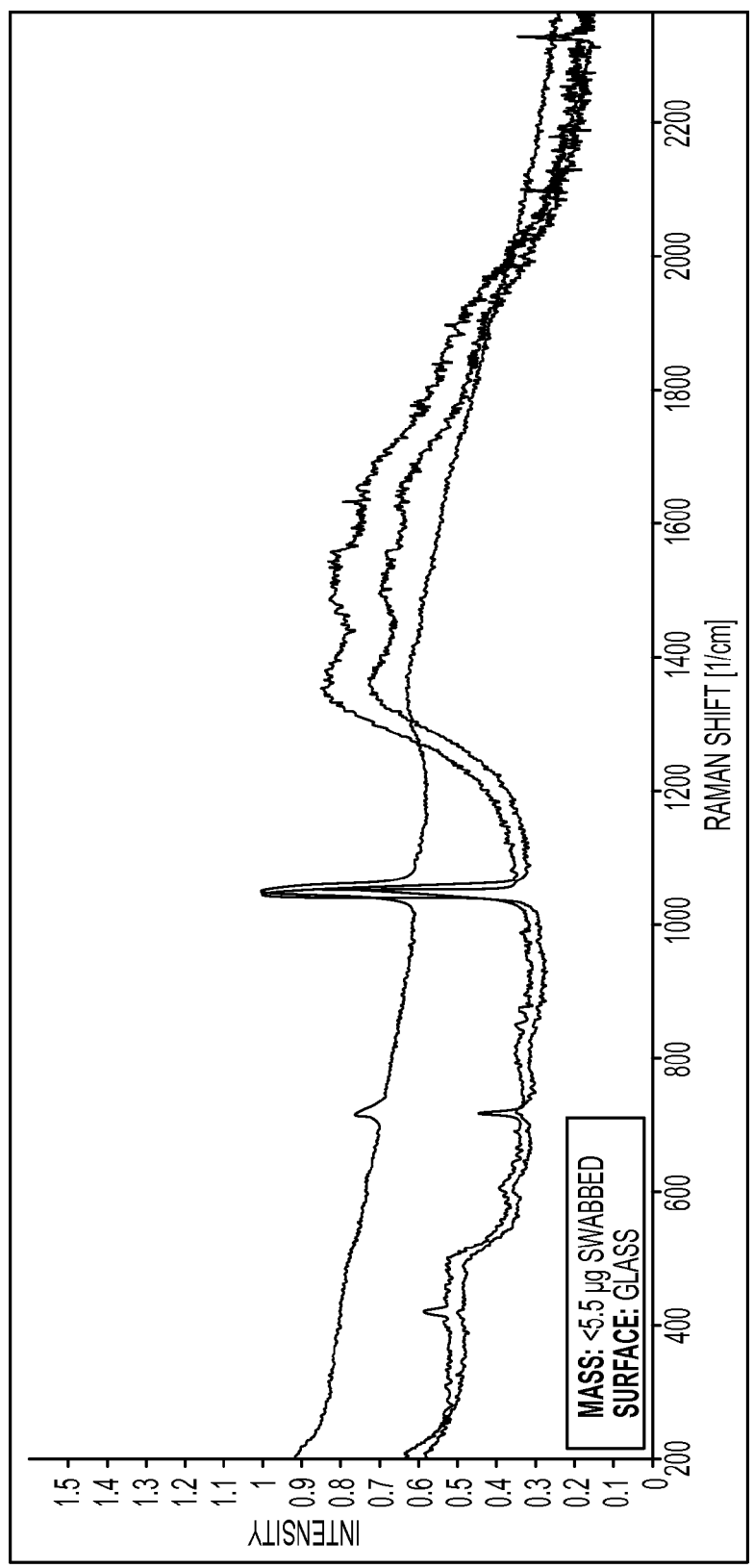
FIG. 14B is a graph of Raman spectral overlay of n=3 replicates of <5 µg solid ammonium nitrate challenges using a swab of glass.

As shown in FIGS. 14A and 14B, the probability of detecting small amounts of a solid chemical challenge such as ammonium nitrate (AN) directly on a surface that has an optically transparent and/or algorithmically filtered signal often obscures the signal attributed to the target analyte. Removing it from the surface by utilizing the swab system with an integral sample collection substrate free of spectroscopic interference eliminates the background signal from the collected spectra resulting in the detection rate when analyzed directly on glass and when swabbed from glass increasing from 0% (FIG. 14A) to 100% (FIG. 14B) respectively.

Additional Downstream Analysis

According to an embodiment, system 10 also provides the benefit of additional analysis of the substrate and sample. Since the collection substrate and sample are sealed within the vial 36, the target analyte can be analyzed by another device or method after analysis by the non-destructive Raman analysis. The sample vial containing target analyte could be, for example, carried, moved, or shipped to another location either close or remote such as a laboratory. Other analytical methods could include, but are not limited to, High Performance Liquid Chromatography ("HPLC"), ion mobility spectrometry ("IMS"), gas chromatograph mass spectrometry ("GC-MS"), and/or Fourier transfer infrared ("FTIR") absorbance spectrometry. For example, preparation of samples for HPLC would result in a simple addition of a desired solvent to the original vial, followed by mixing, extraction, and recapping with a standard septa vial. Liquids or solids could also be used for thermally desorbing the sample into the inlet of other portable and handheld vapor detection instruments, such as an IMS, GC-MS, or FTIR absorbance spectrometer. This is yet another benefit of the substrate 34, as quantitative extraction of collected analytes using organic solvents from the substrate will not result in leaching of binders that can interfere with liquid analytical techniques.

Figure 15:
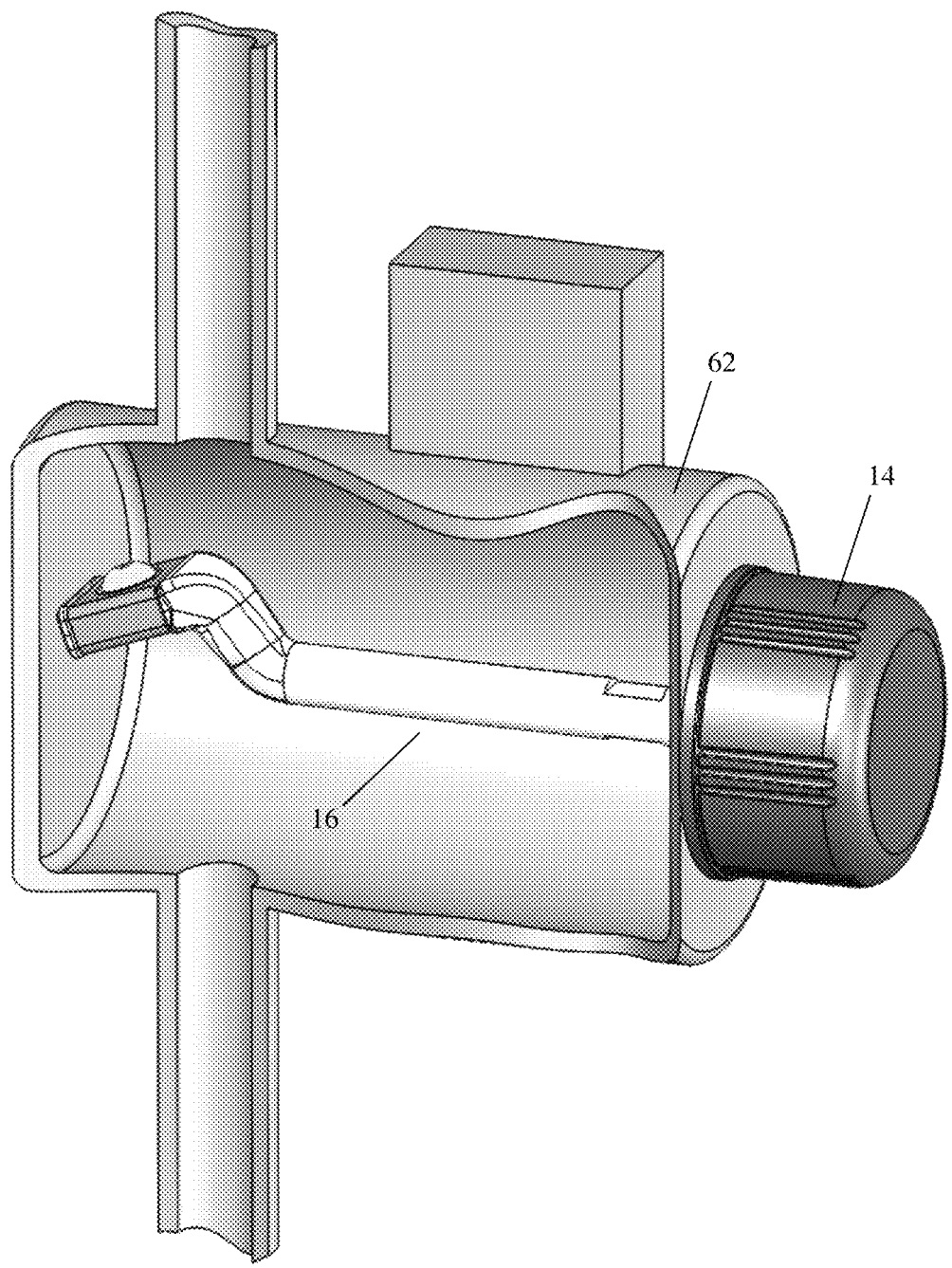
FIG. 15 is a side view of a sample vial and thermal desorption heat block in accordance with an embodiment.

Referring now to FIG. 15, a schematic of a heat chamber 62 tailored to receive the sample swab 16, allowing for thermal desorption of the target analyte from the collection substrate. For example, sample swab 16 can be inserted into a threaded receptacle in the thermal desorption heat block, screwed down against the gasket to provide adequate seal, heat can be applied, and resulting vapor generated from target analytes(s) can be analyzed. This is just one example of the many additional analyses that can be performed by the desorption of the target analyte from the collection substrate.

While various embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings is/are used. Those skilled in the art will recognize, or be able to ascertain using no more than routine experimentation, many equivalents to the specific embodiments described herein. It is, therefore, to be understood that the foregoing embodiments are presented by way of example only and that, within the scope of the appended claims and equivalents thereto, embodiments may be practiced otherwise than as specifically described and claimed. Embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present disclosure.

The above-described embodiments of the described subject matter can be implemented in any of numerous ways. For example, some embodiments may be implemented using hardware, software or a combination thereof. When any aspect of an embodiment is implemented at least in part in software, the software code can be executed on any suitable processor or collection of processors, whether provided in a single device or computer or distributed among multiple devices/computers.

The claims should not be read as limited to the described order or elements unless stated to that effect. It should be understood that various changes in form and detail may be made by one of ordinary skill in the art without departing from the spirit and scope of the appended claims. All embodiments that come within the spirit and scope of the following claims and equivalents thereto are claimed.

What is claimed is:

1. A system for analyzing a sample using spectroscopy, the system comprising:
   a spectroscope;
   a sample vial comprising a swab removably sealable within an enclosure, the enclosure comprising at least one transparent portion to allow transmission of electromagnetic radiation; and
   a sample vial adaptor configured to affix to the spectroscope, and further comprising a sample vial receptacle configured to receive the sample vial, wherein the adaptor is configured to position the sample vial such that the transparent portion of the enclosure is between the swab and a laser of the spectroscope, and such that the swab is positioned at the focal distance of the laser.

2. The system of claim 1, wherein the sample vial adaptor is configured to reversibly affix to the spectroscope.

3. The system of claim 1, wherein the spectroscope comprises a sample chamber, and wherein the sample vial adaptor is configured to insert into the sample chamber of the spectroscope.

4. The system of claim 1, wherein the sample vial further comprises a removable cap with a stem extending outwardly, the stem comprising the swab at the end distal to the cap, and further wherein the stem is suspended in the sample vial when the cap is affixed to the sample vial.

5. The system of claim 4, wherein the stem comprises an angle at the distal end to position the swab at an approximately 20 degree angle compared to the end of the stem proximal the cap.

6. The system of claim 1, wherein the swab comprises an absorbent collection substrate.

7. The system of claim 1, wherein the sample vial comprises a positioning tab, and wherein the sample vial receptacle comprises a positioning slot complementary to the positioning tab of the sample vial.

8. The system of claim 1, wherein the sample vial adaptor further comprises a probe receptacle configured to receive a probe of Raman instrument.

9. A method for analyzing a sample using spectroscopy, the method comprising the steps of:
   providing a transparent sample vial, the sample vial comprising a collection substrate;
   swabbing the collection substrate on a surface to be sampled;
   inserting the collection substrate within the sample vial such that the collection substrate is suspended within the sample vial;
   placing the sample vial in a sample vial receptacle of a sample vial adaptor, wherein the adaptor is affixed to the spectroscope and is configured to position the sample vial such that the swab is positioned at the focal distance of a laser of the spectroscope; and
   analyzing the collection substrate using the spectroscope.

10. The method of claim 9, wherein the adaptor comprises a mounting post configured to insert into a sample chamber of a spectroscope.

11. The method of claim 9, wherein the sample vial comprises a swab removably sealable within an enclosure, the enclosure comprising at least one transparent portion to allow transmission of radiation.

12. The method of claim 11, wherein the sample vial further comprises a removable cap with a stem extending outwardly, the stem comprising the swab at the end distal to the cap, and further wherein the stem is vertically suspended in the sample vial when the cap is affixed to the sample vial.

13. The method of claim 12, wherein the stem comprises an angle at the distal end to position the collection substrate at an approximately 20 degree angle compared to the end of the stem proximal the cap.

14. The method of claim 9, wherein the sample vial comprises a positioning tab, and wherein the sample vial receptacle comprises a positioning slot complementary to the positioning tab of the sample vial.

15. The method of claim 9, wherein the sample vial adaptor comprises a probe receptacle configured to receive a probe of spectroscope.

16. A device for swabbing a surface, the device comprising:
- an enclosure, wherein at least a portion of the enclosure is transparent;
- a cap configured to removably affix to the transparent enclosure; and
- a stem extending outwardly from the cap, the stem comprising a collection substrate at the end distal to the cap, and further comprising an angle at the distal end to position the collection substrate at an angle compared to the end of the stem proximal the cap;
- wherein the stem is suspended in the sample vial when the cap is affixed to the transparent enclosure.

17. The device of claim 16, wherein the collection substrate comprises quartz fiber.

18. The device of claim 16, wherein the angle is approximately 20 degrees.

19. A sample vial adaptor, the adaptor comprising a sample vial receptacle configured to receive a sample vial comprising a swab removably sealable within an at least partially transparent enclosure, wherein the sample vial adaptor is configured to affix to a spectroscope, and further wherein the sample vial adaptor is configured to position the sample vial such that the transparent portion of the enclosure is positioned between the swab and a laser of the spectroscope, and such that the swab is positioned at the focal distance of the laser.

20. A system for analyzing a sample using spectroscopy, the system comprising: a spectroscope; a sample collector comprising a swab at a distal end of a stem; and a sample collector adaptor configured to affix to the spectroscope, and further comprising a sample collector receptacle configured to receive the sample collector, wherein the adaptor is configured to position the swab of the sample collector at the focal distance of a laser of the spectroscope.

21. The system of claim 20, wherein the stem comprises an angle at the distal end to position the swab at an approximately 20 degree angle compared to a proximal end of the stem.

22. The system of claim 20, wherein the swab comprises an absorbent collection substrate.

23. The system of claim 22, wherein the absorbent collection substrate comprises quartz fiber.

24. The system of claim 20, wherein the sample collector comprises a positioning tab, and wherein the sample collector receptacle comprises a positioning slot complementary to the positioning tab of the sample collector.

25. The system of claim 20, wherein the sample collector adaptor further comprises a probe receptacle configured to receive a probe of Raman instrument.

26. A sample collector adaptor, the adaptor comprising a sample collector receptacle configured to receive a sample collector comprising a swab, wherein the sample collector adaptor is configured to affix to a spectroscope, and further wherein the sample collector adaptor is configured to position the sample collector such that the swab is positioned at the focal distance of a laser of the spectroscope.

27. The sample collector adaptor of claim 26, wherein the stem comprises an angle at the distal end to position the swab at an approximately 20 degree angle compared to a proximal end of the stem.

28. The sample collector adaptor of claim 26, wherein the swab comprises an absorbent collection substrate.

29. The sample collector adaptor of claim 28, wherein the absorbent collection substrate comprises quartz fiber.

30. The sample collector adaptor of claim 26, wherein the sample collector receptacle comprises a positioning slot complementary to a positioning tab of the sample collector.

31. The sample collector adaptor of claim 26, wherein the sample collector adaptor further comprises a probe receptacle configured to receive a probe of Raman instrument.

* * * * *